(12) United States Patent
Liao et al.

(10) Patent No.: US 9,643,931 B2
(45) Date of Patent: May 9, 2017

(54) PROCESS FOR PREPARING ENZALUTAMIDE

(71) Applicant: SCINOPHARM TAIWAN, LTD., Tainan (TW)

(72) Inventors: Yuan-Xiu Liao, Tainan (TW); Jiunn-Cheh Guo, Tainan (TW); Wen-Li Shih, Nantou (TW); Shang-Hong Chen, Chiayi (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/177,117

(22) Filed: Jun. 8, 2016

(65) Prior Publication Data
US 2016/0362381 A1 Dec. 15, 2016

Related U.S. Application Data

(60) Provisional application No. 62/173,814, filed on Jun. 10, 2015.

(51) Int. Cl.
*C07D 233/86* (2006.01)
(52) U.S. Cl.
CPC .................. *C07D 233/86* (2013.01)
(58) Field of Classification Search
CPC .................................... C07D 233/86
See application file for complete search history.

(56) References Cited

U.S. PATENT DOCUMENTS

| 7,709,517 B2 | 5/2010 | Sawyers et al. |
| 2013/0116269 A1 | 5/2013 | Ivachtchenko et al. |
| 2015/0210649 A1 | 7/2015 | Dwivedi et al. |

FOREIGN PATENT DOCUMENTS

| CN | 103910679 A | 7/2014 |
| CN | 105461633 A | 4/2016 |
| WO | WO-2010/099238 A1 | 9/2010 |
| WO | WO-2010/118354 A1 | 10/2010 |
| WO | WO-2011/106570 A1 | 9/2011 |

OTHER PUBLICATIONS

Jain, et al. Document No. 155:380335 retrieved from STN, WO 2011106570; Sep. 1, 2011.*
International Search Report mailed on Nov. 1, 2016, for PCT Application No. PCT/SG2016/050267, filed Jun. 8, 2016, 6 pages.
Salerni, O.L. et al. (Sep./Oct. 1999). "Synthesis of bis-3-alkyl-5-arylhydantoins and bis-3-alkyl-5-arylthiohydantoins separated by two and four carbon atoms," *Journal of Heterocyclic Chemistry* 36(5):1179-1182.
Written Opinion mailed on Nov. 1, 2016, for PCT Application No. PCT/SG2016/050267, filed Jun. 8, 2016, 11 pages

* cited by examiner

*Primary Examiner* — Shawquia Jackson
(74) *Attorney, Agent, or Firm* — Mintz, Levin, Cohn, Ferris, Glovsky and Popeo, P.C.

(57) ABSTRACT

The present invention provides a process for the efficient preparation of enzalutamide.

21 Claims, No Drawings

PROCESS FOR PREPARING ENZALUTAMIDE

CROSS-REFERENCES TO RELATED APPLICATIONS

This application claims the benefit of priority under 35 U.S.C. §119(e) to U.S. Provisional Application Ser. No. 62/173,814, filed Jun. 10, 2015, the disclosure of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to a novel process for preparing Enzalutamide which has the chemical name 4-(3-(4-cyano-3-(trifluoromethyl)phenyl)-5,5-dimethyl-4-oxo-2-sulfanylideneimidazolidin-1-yl)-2-fluoro-N-methylbenzamide and is represented by the structure:

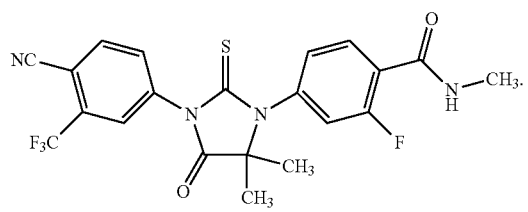 [SMILES: CNC(=O)c1ccc(N2C(=S)N(c3ccc(C#N)c(C(F)(F)F)c3)C(=O)C2(C)C)cc1F]

Enzalutamide (marketed as XTANDI®) is used as an agent for treating castration-resistant prostate cancer and was approved by the U.S. Food and Drug Administration (FDA) on Aug. 31, 2012.

U.S. Pat. No. 7,709,517 (the '517 patent) describes that aniline 1 was reacted with acetone cyanohydrin 2 to lead to compound 3 in 75% yield (Scheme 1). Thiourea 5 was produced after compound 3 was reacted with commercially available isothiocyanate 4. Without isolation, thiourea 5 was subjected to hydrolysis conditions affording enzalutamide in 25% yield after column purification (acetone/DCM (5/95)). The synthetic approach is very limited for industrial application because acetone cyanohydrin 2 has been identified as an extremely hazardous chemical.

Scheme 1: Preparation of Enzalutamide Disclosed in US7709517B2

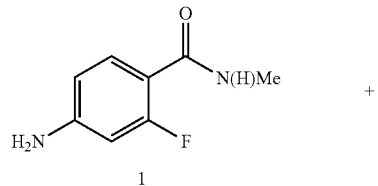

1

+

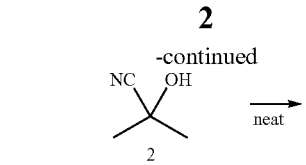

2

→ neat

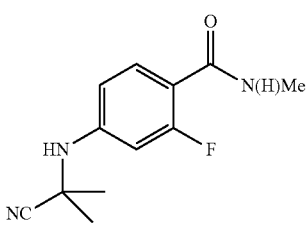

3 (75%)

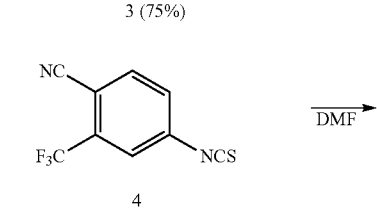

4

→ DMF

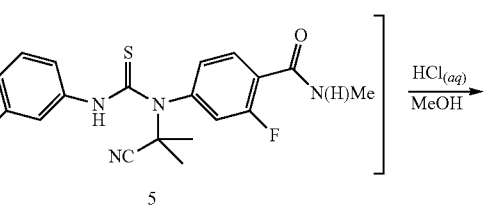

5

→ HCl(aq) / MeOH

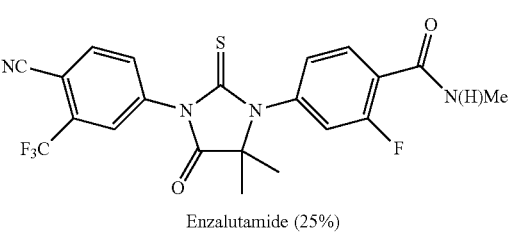

Enzalutamide (25%)

A similar approach for enzalutamide preparation was reported in PCT publication WO2011106570A1 (Scheme 2). Reaction of bromide 6 with amino acid 7 assisted by CuCl, generated compound 8 in 76% yield. Compound 8 was converted to its corresponding ester 9 in 95% yield using MeI and K₂CO₃. Heating a mixture containing ester 9 and isothiocyanate 4 at elevated temperature gave enzalutamide in 82% yield after recrystallization from IPA.

Scheme 2: Preparation of Enzalutamide Disclosed in WO2011106570A1

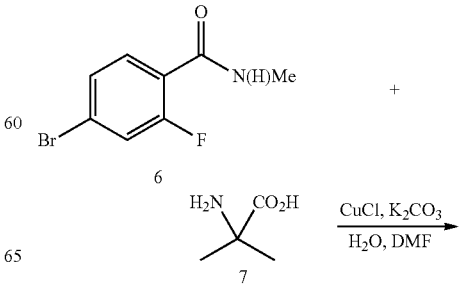

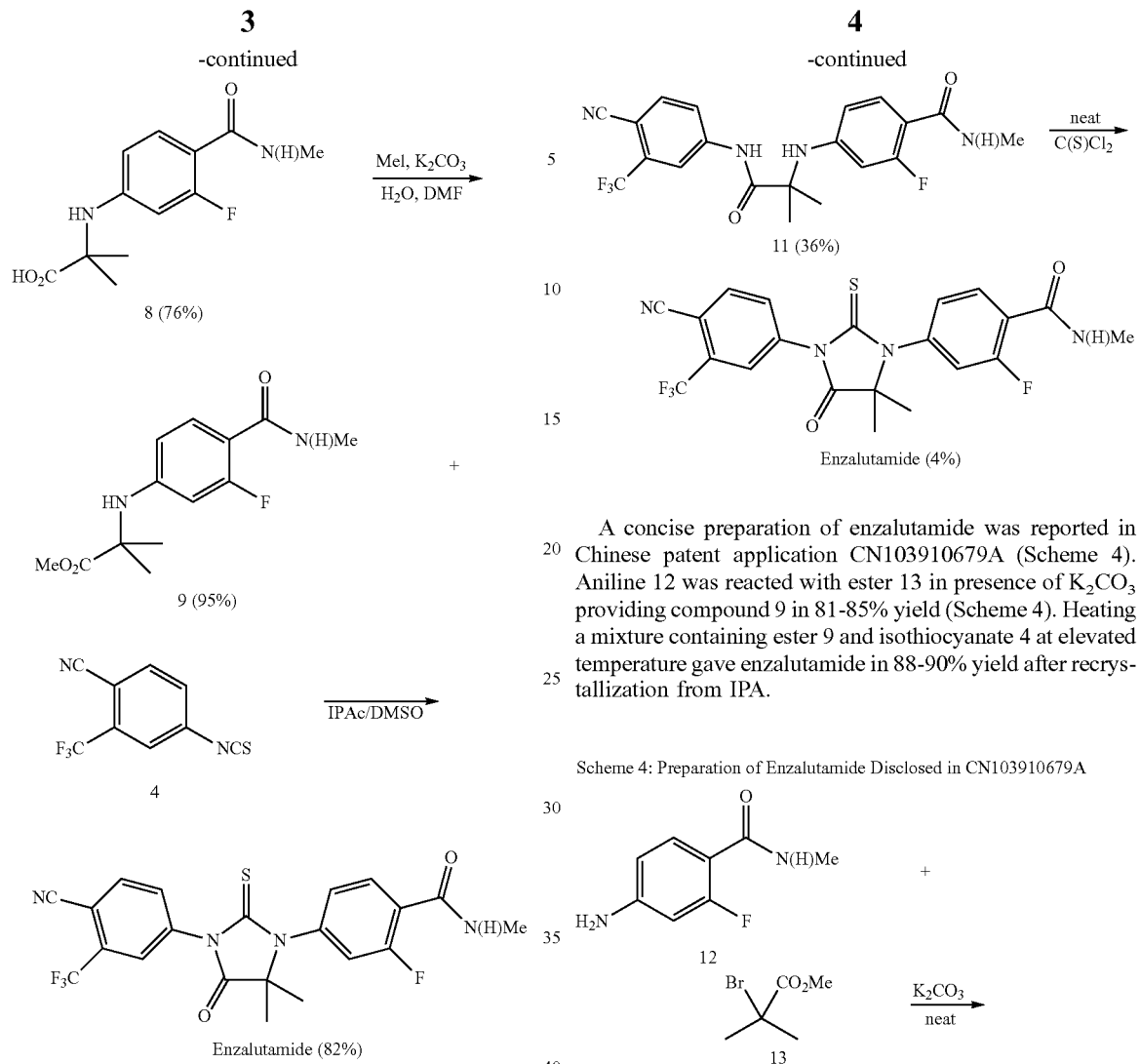

Another synthetic route was also reported in PCT publication WO2011106570A1 (Scheme 3). Briefly, compound 8 was coupled with aniline 10 resulting in the production of compound 11 in 36% yield. Enzalutamide was generated in 4% yield after compound 11 was heated in thiophosgene.

A concise preparation of enzalutamide was reported in Chinese patent application CN103910679A (Scheme 4). Aniline 12 was reacted with ester 13 in presence of $K_2CO_3$ providing compound 9 in 81-85% yield (Scheme 4). Heating a mixture containing ester 9 and isothiocyanate 4 at elevated temperature gave enzalutamide in 88-90% yield after recrystallization from IPA.

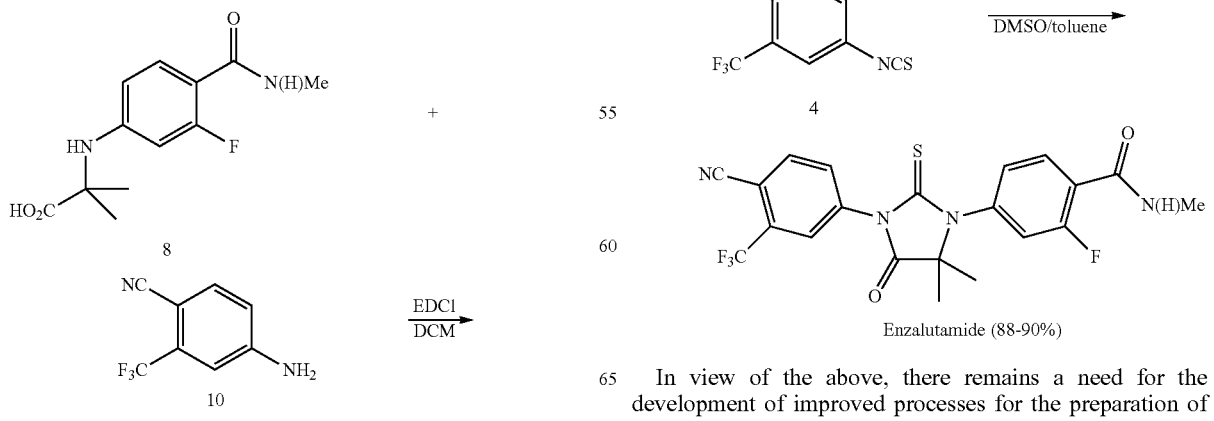

In view of the above, there remains a need for the development of improved processes for the preparation of enzalutamide.

BRIEF SUMMARY OF THE INVENTION

In one aspect, the present invention provides a process for preparing a compound of formula I:

*[Structure of formula I: enzalutamide]* the process comprising reacting the compound of formula II

*[Structure of formula II]* wherein $R^a$ is selected from OH and $NR^1R^2$; wherein $R^1$ and $R^2$ are independently selected from H and $C_1$-$C_8$ alkyl, with a compound of formula III

*[Structure of formula III]* to form the compound of formula I (enzalutamide).

In a second aspect, the present invention provides a process for preparing a compound of formula I:

*[Structure of formula I]* the process comprising reacting a compound of formula IIa:

*[Structure of formula IIa]* wherein $R^1$ and $R^2$ are independently selected from H and $C_1$-$C_8$ alkyl, with a compound of formula III

*[Structure of formula III]* to form the compound of formula I (enzalutamide).

In a third aspect, the present invention provides a process for preparing a compound of formula I:

*[Structure of formula I]* the process comprising:
a) reacting a compound of formula IIb

*[Structure of formula IIb]* with a compound of formula III

*[Structure of formula III]* to produce the compound of formula I; and
b) isolating and purifying and the compound of formula I obtained in step a), wherein the compound of formula I comprises no more than 0.5% by HPLC area percent (A %) of impurity A.

*[Structure of Impurity A]*

$C_{20}H_{18}F_4N_4O_2$
Exact Mass: 422.14
Mol. Wt.: 422.38
Impurity A

BRIEF DESCRIPTION OF THE DRAWINGS

Not Applicable

DETAILED DESCRIPTION OF THE INVENTION

General

The invention herein provides a novel and mild scheme for the preparation of enzalutamide. The present invention avoids using the toxic reagents, cyanohydrin and methyl iodide, and the reaction temperature is kept at or below room temperature. Moreover, the present invention provides a better conversion yield of enzalutamide and also reduces the formation of impurity A.

Definitions

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e., $C_1$-$C_8$ means one to eight carbons), although such designators may be omitted. Unless otherwise specified, the alkyl groups of the present invention contain 1 to 10 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the terms "reacting" and "contacting" refer to the process of bringing into contact at least two distinct species such that they can react. It should be appreciated, however, that the resulting reaction product can be produced directly from a reaction between the added reagents or from an intermediate from one or more of the added reagents that can be produced in the reaction mixture. As used herein, the term "treating" refers to contacting a substance with at least one other substance.

As used herein, the term "solvent" refers to a substance that is liquid at ambient temperature and pressure. Examples of solvents include water, and organic solvents such as acetone, toluene, methylene chloride (DCM), ethyl acetate (EtOAc), acetonitrile (MeCN), tetrahydrofuran (THF), benzene, chloroform (CHCl$_3$), diethyl ether (Et$_2$O), dimethyl formamide (DMF), dimethyl sulfoxide (DMSO), dimethyl acetamide (DMAc), methanol (MeOH), ethanol (EtOH), isopropanol or isopropyl alcohol (IPAc), and petroleum ether. Organic solvent mixtures include combinations of two, three, four or more, of the noted organic solvents.

As used herein, the term "base" refers to a molecule that is capable of accepting a proton (i.e., a hydrogen cation) to form a conjugate acid of the base. Examples of bases include, but are not limited to, Hunig's base (i.e., N,N-diisopropylethylamine), lutidines including 2,6-lutidine (i.e., 2,6-dimethylpyridine also sometimes referred to a lutidine), triethylamine, and pyridine.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed. The following schemes are provided as embodiments to illustrate, but not to limit the present invention.

Embodiments of the Invention

The present invention provides a new process for preparing enzalutamide (see formula I).

In one aspect, the present invention provides a process for preparing a compound of formula I:

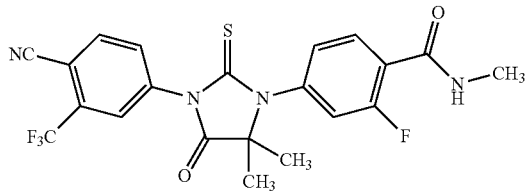

the process comprising reacting a compound of formula II

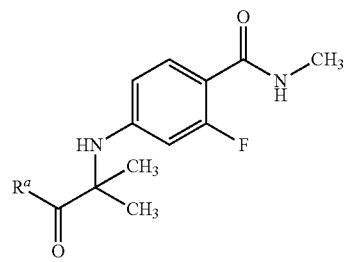

wherein $R^a$ is selected from —OH and —NR$^1$R$^2$; wherein R$^1$ and R$^2$ are independently selected from H and $C_1$-$C_8$ alkyl, with a compound of formula III

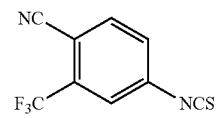

under conditions sufficient to provide the compound of formula I.

In general, reacting the compound of formula II with the compound of formula III can be accomplished under mild conditions using an excess (on a molar or equivalent basis) of compound III relative to compound II. The reaction can be monitored by conventional methods, and additional amounts of III can be added to facilitate a complete reaction producing compound I. The reaction is generally carried out in an organic solvent, typically a dried solvent which is aprotic. Suitable solvents include, but are not limited to DMSO, toluene, dimethylacetamide (DMAc), isopropyl acetate (IPAc), acetonitrile (MeCN), and the like, as well as mixtures thereof.

Depending on the temperature, the amount and concentration of the reactants, the reaction is often conducted at ambient temperatures (20° C. to 30° C.), though elevated temperatures can also be used, as well as reduced temperatures. Accordingly, the reaction can be conducted at, for example, temperatures of 10° C. to 90° C., 20° C. to 80° C., 25° C. to 70° C., 10° C. to 50° C., 40° C. to 80° C., 50° C. to 70° C., 40° C. to 60° C., or 20° C. to 30° C. Alternatively, the reaction can be carried out in stages, at initial temperatures of 0° C. to 20° C., or 10° C. to 30° C., followed by more elevated temperatures in some of the ranges noted above.

Isolation of the product, compound I, is generally carried out using standard work up conditions in which the product mixture is partitioned between an organic and aqueous solvent mixture, with the product separated from the aqueous portion and isolated after removal of the organic solvent or solvent mixture.

In another aspect, the present invention provides a process for preparing a compound of formula I:

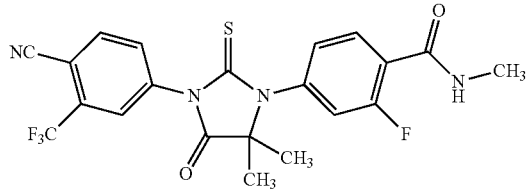

I the process comprising reacting a compound of formula IIa:

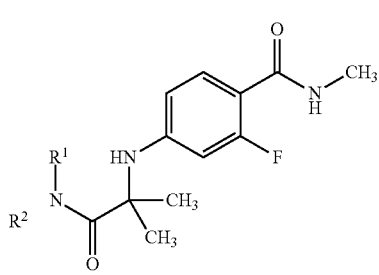

IIa wherein $R^1$ and $R^2$ are independently selected from H and $C_1$-$C_8$ alkyl, with a compound of formula III

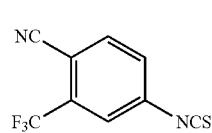

III under conditions sufficient to form the compound of formula I.

In some embodiments, $R^1$ is H and $R^2$ is ethyl. In some embodiments, the reaction is conducted in the organic solvent. In some embodiments, the organic solvent is selected from DMSO/toluene, DMSO/IPAc, DMSO, DMAc and MeCN. In some embodiments, the organic solvent is MeCN. In some embodiments, the reaction is conducted at a temperature above 50° C. In some embodiments, the reaction temperature is 60-70° C.

In some embodiments, the compound of formula IIa is prepared from the compound of formula IIb by reacting with an amine, such as $HNR^1R^2$.

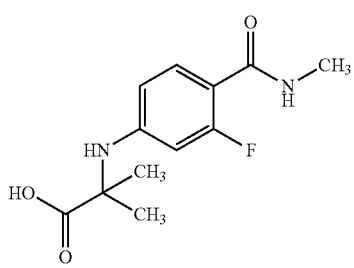

IIb

In some embodiments, the amine is selected from primary amine. In some embodiments, the primary amine is ethylamine.

In a related aspect, the present invention provides a process for preparing a compound of formula I:

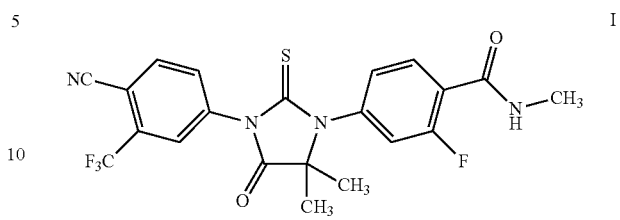

I the process comprising:
a) reacting a compound of formula IIb

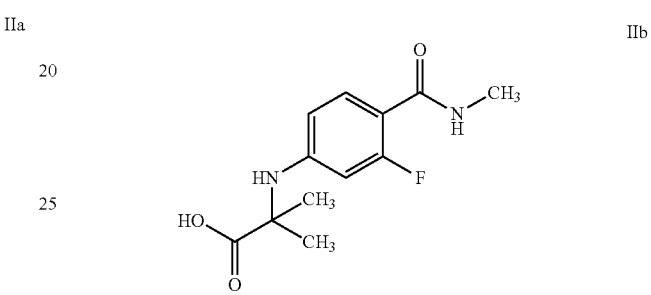

IIb with a compound of formula III

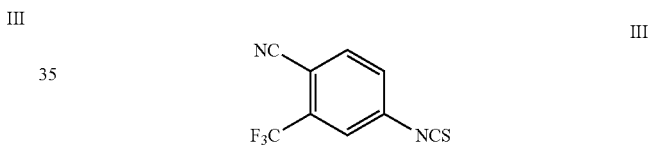

III to produce the compound of formula I; and
b) isolating and purifying and the compound of formula I obtained in step a), wherein the compound of formula I comprises no more than 0.5% by HPLC area percent (A %) of impurity A

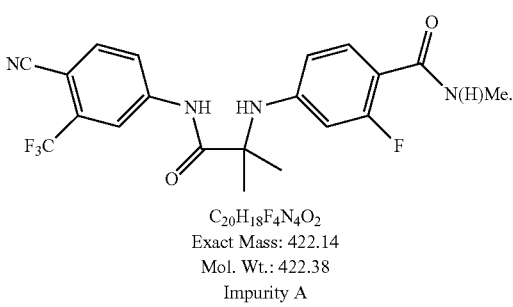

$C_{20}H_{18}F_4N_4O_2$
Exact Mass: 422.14
Mol. Wt.: 422.38
Impurity A

The HPLC evaluation to quantify the amounts of impurity A can be conducted according to a number of methods known to those of skill in the art. In one embodiment, the amount of impurity A is determined using an Agilent Zorbax SB-C18 column (4.6 mm*150 mm, 3.5 um) with a mobile phase of MeCN, 0.1% $H_3PO_{4(aq)}$.

In some embodiments, the reaction is conducted at a temperature of below 30° C., for example, from 0° C. to 25°

C., or from 5° C. to 20° C., or from 5° C. to 15° C. In some embodiments, the temperature is about 10° C. In some embodiments, the reaction is conducted with a base. A variety of bases are useful in this aspect of the invention, including for example, NaOH, KOH, tertiary amine bases (e.g., trimethylamine, diisopropylethylamine) and the like. In some embodiments, the base is NaOH. In some embodiments, the synthetic steps described above can be carried out in an organic solvent, such as THF, or any other suitable solvent as described above. Mixtures of solvents can also be used. In some embodiments, the ratio of THF/NaOH is 8/1 (v/v). In some of these embodiments, with volume amounts of NaOH, a selected amount is an aqueous solution of NaOH, that is about 23.9% of NaOH in water.

In some embodiments, the compound of formula I comprises no more than 0.3% by HPLC area percent (A %) of impurity A. In some embodiments, the compound of formula I comprises no more than 0.1% by HPLC area percent (A %) of impurity A. In some embodiments, the content of impurity A is not detectable, when measured according to the HPLC method described above.

As noted above, the compound IIa can be prepared from compound IIb, by coupling an amine (HNR$^1$R$^2$) with the acid IIb. A variety of amide-forming reactions and conditions are suitable. Scheme 5 illustrates the preparation using a primary amine (ethylamine), EDCI (1-ethyl-3-(3-dimethylaminopropyl)carbodiimide) and HOBt (hydroxybenzotriazole).

In Scheme 5, acid 8 was reacted with ethylamine (in THF or aqueous solution) in the presence of EDCI and HOBt affording amide 14 in 61-65% yield (Table 1).

Scheme 5: Preparation of Enzalutamide from Amide 14

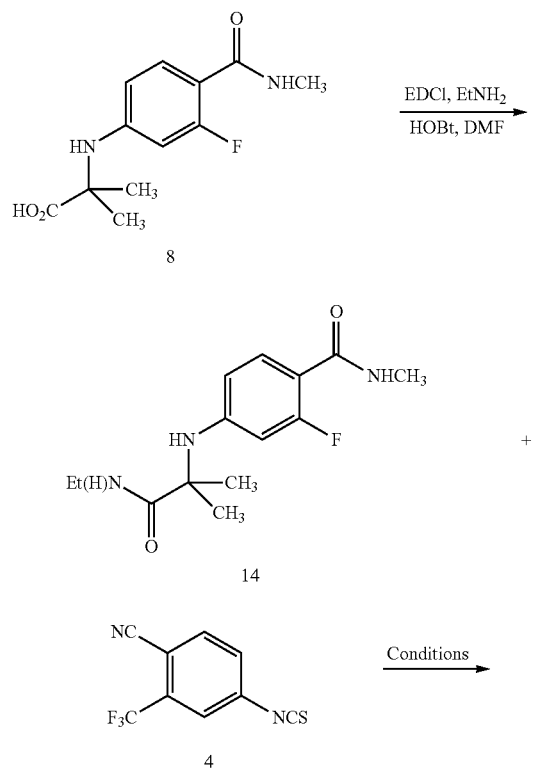

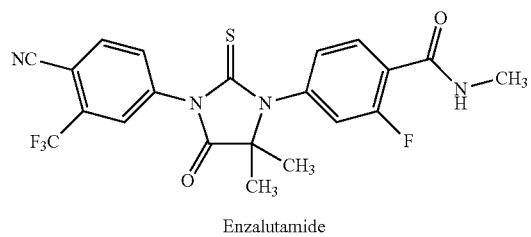

Enzalutamide

TABLE 1

Results of Amide 14 Formation

| Entry | 1 | 2 |
|---|---|---|
| Acid 8 (g, equiv) | 10, 1 | 10, 1 |
| EDCI (g, equiv) | 7.33, 1.2 | 7.33, 1.2 |
| HOBt (g, equiv) | 7.2, 1.2 | 7.2, 1.2 |
| DMF (mL, vol) | 50, 5 | 50, 5 |
| EtNH$_2$ (mL, equiv) | 2M in THF (49, 2.5) | 70% in H$_2$O (15.7, 5) |
| Amide 14 (g, %) | 6.72, 61 | 7.13, 65 |

Enzalutamide formation was achieved from amide 14 and isothiocyanate 4 at 50-60° C. in different solvent systems (Table 2). Enzalutamide was obtained in 31-39% when the reaction was conducted in DMSO/toluene, DMSO/IPAc, DMSO, or DMAc (Entry 1-4).

TABLE 2

Results of Enzalutamide Formation

| Entry | 1 | 2 | 3 | 4 |
|---|---|---|---|---|
| Amide 14 (g, equiv) | 0.5/1 | 0.5/1 | 0.5/1 | 0.5/1 |
| Isothiocyanate 4 (g, equiv) | 0.89, 2.2 | 0.89, 2.2 | 0.89, 2.2 | 0.89, 2.2 |
| Solvent | DMSO/toluene | DMSO/IPAc | DMSO | DMAc |
| Volume (mL) | 2.5 (2/3, v/v) | 2 (1/1, v/v) | 2 | 2 |
| Temperature (° C.) | 50-60 | 50-60 | 50-60 | 50-60 |
| Enzalutamide (%) | 38 | 31 | 39 | 32 |

It was found that a slightly better yield at 51% could be obtained when the reaction was conducted in MeCN at 50-60° C. (Table 3, Entry 1). The yield could be further improved to 69% (Entry 2) using more isothiocyanate 4 (5.4 vs. 2.2 equiv) at higher temperature (60-70 vs. 50-60° C.)

TABLE 3

Results of Enzalutamide Formation

| Entry | 1 | 2 |
|---|---|---|
| Amide 14 (g, equiv) | 0.5, 1 | 0.5, 1 |
| Isothiocyanate 4 (g, equiv) | 0.89, 2.2 | 2.19, 5.4 |
| MeCN (mL) | 2 | 2 |
| Temperature (° C.) | 50-60 | 60-70 |
| Enzalutamide (%) | 51 | 69 |

Another synthetic route was established to produce enzalutamide as shown in Scheme 6.

Scheme 6: Preparation of Enzalutamide from Acid 8

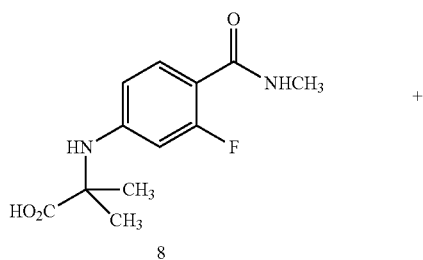

8

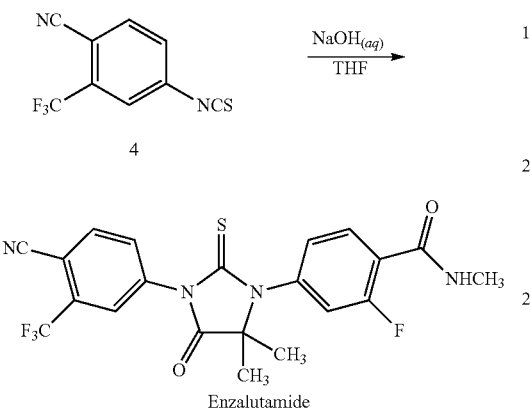

Enzalutamide

The first reaction was carried out by treating acid 8 with isothiocyanate 4 (3.6 equiv) in a mixture of NaOH(aq)/THF at 20-30° C. (Table 5). Enzalutamide was isolated in 53.7% yield after workup followed by recrystallization from IPA. These newly established reaction conditions are considered friendlier compared with those reported (U.S. Pat. No. 7,709,517B2, WO2011106570A1 and CN103910679A).

TABLE 5

Results of cyclization reaction (acid approach)

| | |
|---|---|
| Acid 8 (g, equiv) | 0.3, 1 |
| Isothiocyanate 4 (g, equiv) | 0.97, 3.6 |
| 2N NaOH(aq) (mL, equiv) | 0.89, 1.5 |
| THF (mL) | 1.5 |
| Temperature (° C.) | 20-30 |
| Enzalutamide (%) | 53.7 |

In another aspect, the use of a NaOH$_{(aq)}$/THF system for the preparation of enzalutamide provided a better conversion yield of enzalutamide and can also reduce the formation of impurity A (MW 422).

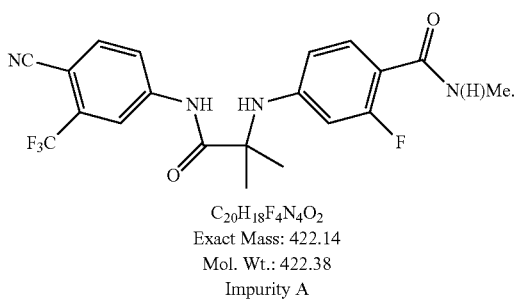

$C_{20}H_{18}F_4N_4O_2$
Exact Mass: 422.14
Mol. Wt.: 422.38
Impurity A

Certain specific aspects and embodiments of the invention will be explained in more detail with reference to the following examples, which are provided for purposes of illustration only and should not be constructed as limiting the scope of the invention in any manner.

EXAMPLES

The following abbreviations are used herein:
examples are provided to further illustrate, but not to limit this invention.

Example 1

Preparation of di-amide 14

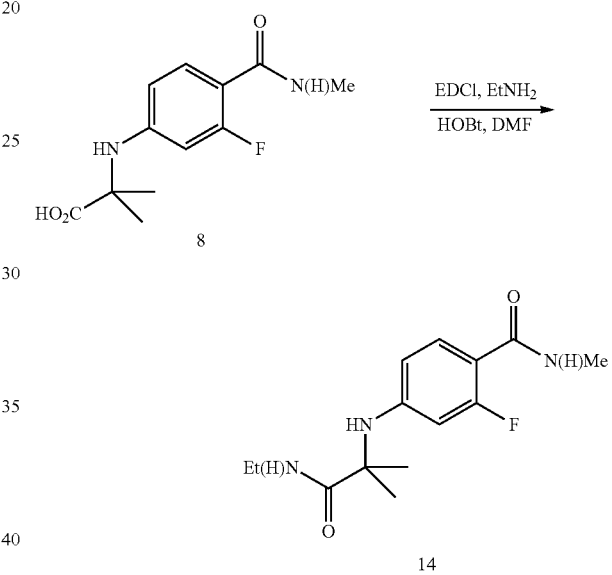

A four-necked round bottom flask was equipped with a mechanical stirrer and a thermometer. To the flask was added compound 8 (10 g, 39.39 mmol, 1 eq), EDCI (7.33 g, 47.2 mmol, 1.2 eq), HOBt (7.20 g, 47.3 mmol, 1.2 eq) and DMF (50 mL, 5 vol) at 20-30° C. under nitrogen. The mixture was stirred at 20-30° C. for 5 min, then EtNH$_2$ (2M in THF, 49 mL, 98 mmol, 2.5 eq) was added to the reaction flask. The reaction mixture was stirred at 20-30° C. for 15 hr. After the reaction was complete, EtOAc (100 mL, 10 vol) and saturated NH$_4$Cl(aq) (100 mL, 10 vol) was added to the reaction mixture and stirring was continued for 5 min. The resulting mixture was filtered, and the filtrate was added to H$_2$O (50 mL). The organic portion was drawn off, and the aqueous layer was washed with EtOAc (3×50 mL, 5 vol). The combined organic portions were concentrated to dryness to obtain about 7 g of crude compound 14 as the yellow oil. To this yellow oil was added EtOAc (5 mL, 0.5 vol) and n-heptane (30 mL, 3 vol) to perform a solvent swap, two times. The solution became a yellow slurry after the completed solvent swap. The solid was filtered off and washed with n-heptane (10 mL, 1 vol) to obtain pure compound 14 in 60.6% yield as an off white solid.

Example 2

Cyclization reaction: amide approach

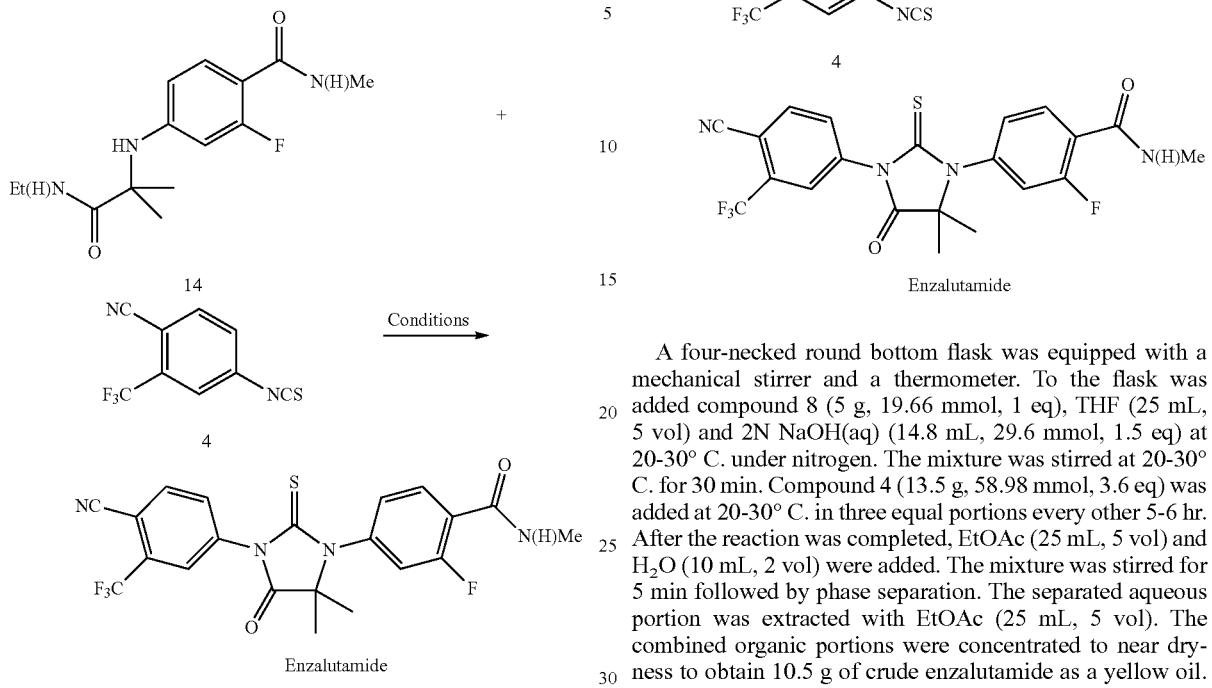

A four-necked round bottom flask was equipped with a mechanical stirrer and a thermometer. To the flask was added compound 14 (0.5 g, 2 mmol, 1 eq), compound 4 (0.89 g, 3.9 mmol, 2.2 eq), 3A molecular sieves (0.5 g, 1 wt) and MeCN (2 mL, 4 vol) at 20-30° C. under nitrogen. The reaction mixture was stirred at 20-30° C. to remove water. After 16 hr, the reaction mixture was warmed to 60-70° C. for 24 hr. Another amount of compound 4 (1.29 g, 5.66 mmol, 3.2 eq, two times) was added and stirring was continued for another 24 hr. After the reaction was complete, EtOAc (10 mL, 20 vol), H$_2$O (10 mL, 20 vol) and saturated NaCl(aq) (5 mL, 10 vol) were added to the reaction mixture and stirring was continued for 5 min. The mixture was filtered, followed by phase separation. The separated aqueous layer was extracted with EtOAc (50 mL, 5 vol). The combined organic portions were concentrated to near dryness obtaining 1.31 g of crude enzalutamide as a yellow oil. To the yellow oil was added IPA (5 mL, 10 vol) and the mixture was heated to 40-50° C. achieving a homogeneous solution. The mixture was cooled to 20-30° C. and stirred for 16 hr. The yellow slurry was filtrated and the filtered cake was washed with IPA (5 mL, 10 vol) to obtain enzalutamide (0.39 g) in 47.3% yield.

Example 3

Cyclization reaction: acid approach

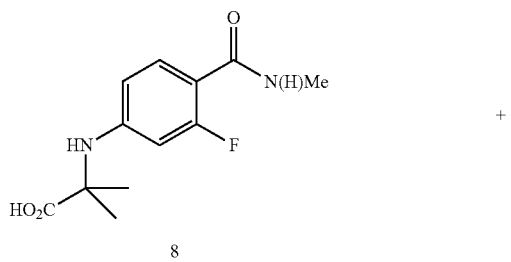

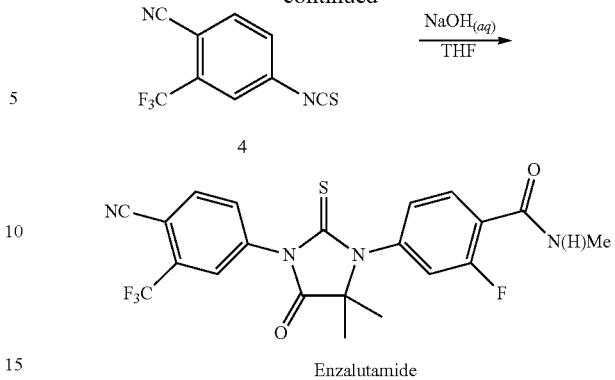

A four-necked round bottom flask was equipped with a mechanical stirrer and a thermometer. To the flask was added compound 8 (5 g, 19.66 mmol, 1 eq), THF (25 mL, 5 vol) and 2N NaOH(aq) (14.8 mL, 29.6 mmol, 1.5 eq) at 20-30° C. under nitrogen. The mixture was stirred at 20-30° C. for 30 min. Compound 4 (13.5 g, 58.98 mmol, 3.6 eq) was added at 20-30° C. in three equal portions every other 5-6 hr. After the reaction was completed, EtOAc (25 mL, 5 vol) and H$_2$O (10 mL, 2 vol) were added. The mixture was stirred for 5 min followed by phase separation. The separated aqueous portion was extracted with EtOAc (25 mL, 5 vol). The combined organic portions were concentrated to near dryness to obtain 10.5 g of crude enzalutamide as a yellow oil. To the yellow oil was added IPA (50 mL, 10 vol), and the mixture was heated to 50-60° C. achieving a homogeneous solution. The mixture was cooled to 20-30° C. and stirred for 1 hr. The yellow slurry was filtered and the filtered cake was washed with IPA (5 mL, 10 vol). The combined filtrate and wash was concentrated to a volume of about 35 mL. The mixture was stirred at 20-30° C. for 16 hr. More IPA (30 mL) was added and the mixture was heated to 50-60° C., achieving a homogeneous solution. The mixture was cooled to 20-30° C. and stirred for 16 hr. The yellow slurry was filtered and the filtered cake was washed with IPA (10 mL×2) to afford enzalutamide (4.8 g) in 52.5% yield.

The volume of water affected the decomposition of compound 4 and the formation rates of impurity A. Two new runs were conducted using different ratios of H$_2$O/THF (Table 6). When a mixture of THF/H$_2$O (9 vol, 6/3, v/v) was used, conversion yield of enzalutamide was 81.7% and content of impurity A was 9.4% (Entry 1). When a mixture of THF/H$_2$O (9 vol, 8/1, v/v) was used, conversion yield of enzalutamide was 87.3% and content of impurity A was 7.4% (Entry 2). Therefore, a mixture of THF/H$_2$O (9 vol, 8/1, v/v) was selected as the solvent system.

TABLE 6

Results for Enzalutamide Formation Studies (Ratio of THF/H$_2$O Studies)

| Entry | 1 | 2 |
|---|---|---|
| THF/H$_2$O (9 vol, v/v) | 6/3 | 8/1 |
| Compound 4 (equiv) | 6 | 3.6 |
| Time (hr) | 116 | 99 |
| Convsersion yield (%) | 81.7 | 87.3 |
| Impurity A (%) | 9.42 | 7.4 |

Table 7 below provides the results conducted by using different amounts of NaOH. When 1.0 equivalent of NaOH was used, conversion yield of enzalutamide was 83.3% but content of the impurity A increased to 23.5% (Entry 1). When 2.0 equivalents of NaOH were used, the conversion yield of enzalutamide slightly decreased to 76.3% and content of the impurity A was greatly reduced to 6.5% (Entry 2). When 3.0 equivalents of NaOH were used, the conversion yield of enzalutamide was 48.1% and content of the impurity A was 9.0% (Entry 3). Therefore, 2.0 equiv of NaOH appeared to be optimal.

TABLE 7

Results for Enzalutamide Formation Studies (Equiv of NaOH Studies)[a]

| Entry | 1 | 2 | 3 |
|---|---|---|---|
| NaOH (equiv) | 1 | 2 | 3 |
| Time (hr) | 66 | 66 | 42.5 |
| Convsersion yield (%) | 83.3 | 76.3 | 48.1 |
| Impurity A (%) | 23.5 | 6.5 | 9.0 |

[a]in THF/H2O (9 vol, 8/1 (v/v)).

Table 8 below summarizes the production of enzalutamide by using different solvents.

TABLE 8

Different solvent used for Enzalutamide Formation

| En-try | Solvent | Base (equiv) | Compound 4 Adding Time (hr) | (equiv) | Time (hr) | Enzalut-amide (%) | Impu-rity A (%) |
|---|---|---|---|---|---|---|---|
| 1 | THF | NaOH (1.5) | 0 | 1.2 | 2 | 10 | 3 |
|   |     |              | 3 | 1.2 | 6.5 | 24 | 4 |
|   |     |              | 7.5 | 1.2 | 24 | 54 | 6 |
| 2 | THF | NaOH (1.5) | 0 | 1.2 | 3 | 28 | 14 |
|   |     |              | 3.5 | 1.2 | 5 | 70 | 13 |
|   |     |              |     |     | 20 | 63 | 10 |
|   |     |              | 21 | 1.2 | 25 | 79 | 11 |
| 3 | THF | NaOH (1.5) | 0 | 3.6 | 2 | 55 | 5.5 |
|   |     |              |   |     | 4 | 54 | 5 |
|   |     |              |   |     | 22 | 58 | 5.5 |
| 4 | THF | NaOH (1.5) | 0 | 1.2 | 2 | 18 | 46 |
|   |     |              |   |     | 4 | 24 | 52 |
|   |     |              |   |     | 22 | 14 | 75 |
|   | THF | K2CO3 (1.5) | 0 | 1.2 | 2 | 23 | 67 |
|   |     |              |   |     | 4 | 14 | 63 |
|   |     |              |   |     | 23 | 32 | 56 |
| 5 | 2-Me—THF | NaOH (1.5) | 0 | 1.2 | 2 | 5 | 4 |
|   |     |              | 4 | 1.2 | 6 | 40 | 4.7 |
|   |     |              | 6.5 | 1.2 | 7.5 | 75 | 8 |
|   |     |              |     |     | 24 | 66 | 7 |
| 6 | DMSO | 2N KOH (1.5) | 0 | 3.6 | 5 | 22 | 27 |
|   |     |              |   |     | 21 | 22 | 26 |
|   | DMAc | 2N KOH (1.5) | 0 | 3.6 | 5 | 18 | 20 |
|   |     |              |   |     | 21 | 25 | 27 |
| 7 | Acetone | NaOH (0.5) | 0e | 1.2 | 3 | 20 | 10 |
|   |     |              |   |     | 8 | 33 | 14 |
|   |     |              | 8 | 1.2 | 23 | 55 | 16 |
|   | ACN | NaOH 0.5 | 0e | 1.2 | 3 | 7.5 | 7 |
|   |     |              |   |     | 8 | 29 | 16 |
|   |     |              | 8 | 1.2 | 23 | 48 | 14 |

Table 9 below shows that using NaHCO3 as base for the preparation of enzalutamide.

TABLE 9

Using NaHCO3 as base for Enzalutamide Formation

| Entry | Solvent | NaHCO3 (sat.) (part) | Compound 4 (equiv) | Time (h) | IPC (hr) | Com-pound 8 (%) | Enzalut-amide (%) |
|---|---|---|---|---|---|---|---|
| 1 | 2-MeTHF | 5 | 1.2 | 0 | 6 | 91 | 9 |
|   |         |   | 1.2 | 6.5 | 21 | 77 | 28 |
| 2 | DCM | 5 | 1.2 | 0 | 6 | 99.8 | 0.1 |
|   |     |   | 1.2 | 6.5 | 21 | 99.2 | 0.8 |

According to the abovementioned results, using NaOH/THF as the reaction condition allows for the production of enzalutamide with higher purity and less impurity.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing a compound of formula I:

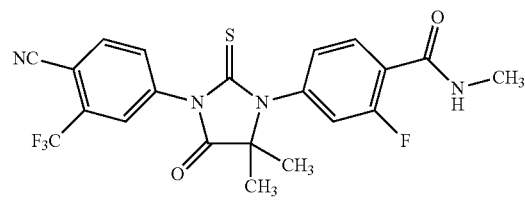

said process comprising reacting a compound of formula IIa:

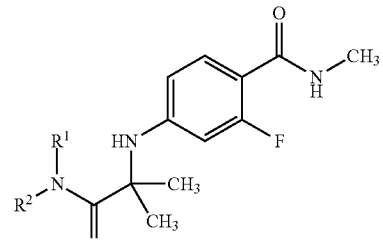

wherein $R^1$ and $R^2$ are independently selected from H and $C_1$-$C_8$ alkyl, with a compound of formula III

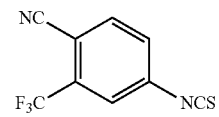

to form said compound of formula I.

2. A process according to claim 1, wherein R¹ is H and R² is ethyl.

3. A process according to claim 1, wherein reacting IIa and III is conducted in an organic solvent or organic solvent mixture.

4. A process according to claim 3, wherein the organic solvent or organic solvent mixture is selected from the group consisting of DMSO/toluene, DMSO/IPAc, DMSO, DMAc and MeCN.

5. A process according to claim 4, wherein the organic solvent is MeCN.

6. A process according to claim 1, reacting IIa and III is conducted in an organic solvent or organic solvent mixture at a temperature above 50° C.

7. A process according to claim 6, wherein the organic solvent or organic solvent mixture is at a temperature of about 60-70° C.

8. A process according to claim 1, further comprising forming said compound of formula IIa by reacting a compound of formula IIb

[Structure IIb]

with an amine of formula HNR¹R².

9. A process according to claim 8, wherein the amine is a primary amine.

10. A process according to claim 9, wherein the primary amine is ethylamine.

11. A process for preparing a compound of formula I:

[Structure I]

said process comprising:
a) reacting a compound of formula IIb

[Structure IIb]

with a compound of formula III

[Structure III]

to produce said compound of formula I; and
b) isolating and purifying and the compound of formula I obtained in step a), wherein the compound of formula I comprising no more than 0.5% by HPLC area percent (A %) of impurity A

[Structure Impurity A]

$C_{20}H_{18}F_4N_4O_2$
Exact Mass: 422.14
Mol. Wt.: 422.38
Impurity A

12. A process according to claim 11, wherein the reacting is conducted at a temperature of about 10° C.

13. A process according to claim 11, wherein the reacting is conducted with a base.

14. A process according to claim 13, wherein the base is NaOH.

15. A process according to claim 11, wherein the reacting is conducted in an organic solvent.

16. A process according to claim 15, wherein the organic solvent is THF.

17. A process according to claim 11, wherein the base is NaOH and the organic solvent is THF.

18. A process according to claim 11, wherein the compound of formula I comprises no more than 0.1% by HPLC area percent (A %) of impurity A.

19. A process for preparing a compound of formula I:

[Structure I]

said process comprising reacting a compound of formula II

[Structure II]

wherein $R^a$ is selected from —OH and —NR$^1$R$^2$; wherein R$^1$ and R$^2$ are independently selected from H and C$_1$-C$_8$ alkyl, with a compound of formula III

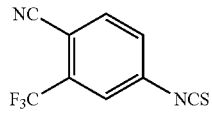

to produce said compound of formula I.

20. A process according to claim 11, wherein the reacting is conducted at a temperature of about 10° C., with THF and aqueous NaOH, wherein the ratio of THF/aqueous NaOH is 8/1 v/v, and the aqueous NaOH is about 23.9% NaOH in water, and wherein the compound of formula I comprises no more than 0.1% by HPLC area percent (A %) of impurity A.

21. A process according to claim 1, wherein R$^1$ is H and R$^2$ is ethyl; reacting IIa and III is conducted in MeCN at a temperature above 50° C.; and further comprising forming said compound of formula IIa by reacting a compound of formula IIb

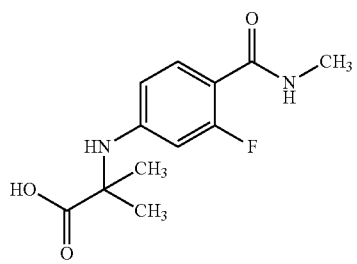

with ethylamine.

* * * * *